United States Patent
Filippo

(10) Patent No.: US 12,268,652 B2
(45) Date of Patent: *Apr. 8, 2025

(54) METHOD FOR PREVENTING OR LIMITING PROGRESSION OF MYOPIA

(71) Applicant: Cataltheia Group, Inc., Wilmington, DE (US)

(72) Inventor: Alessandro Filippo, Varmo (IT)

(73) Assignee: Cataltheia Group, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/219,979

(22) Filed: Jul. 10, 2023

(65) Prior Publication Data

US 2023/0350231 A1 Nov. 2, 2023

Related U.S. Application Data

(63) Continuation of application No. 17/057,171, filed as application No. PCT/IB2019/054016 on May 15, 2019.

(30) Foreign Application Priority Data

May 22, 2018 (IT) ........................ 102018000005599

(51) Int. Cl.
*A61F 9/00* (2006.01)
*A61H 35/02* (2006.01)
*G02C 7/04* (2006.01)

(52) U.S. Cl.
CPC ............ *A61H 35/02* (2013.01); *A61F 9/0008* (2013.01); *G02C 7/047* (2013.01); *G02C 7/049* (2013.01); *G02C 2202/24* (2013.01)

(58) Field of Classification Search
CPC ................................. G02C 7/047; G02C 7/049
(Continued)

(56) References Cited

U.S. PATENT DOCUMENTS

| 3,710,796 A | * | 1/1973 | Neefe | A61F 9/0017 |
| | | | | 351/159.33 |
| 4,466,705 A | * | 8/1984 | Michelson | G09B 23/30 |
| | | | | 351/159.33 |

(Continued)

FOREIGN PATENT DOCUMENTS

| CN | 103576337 B | 1/2018 |
| CN | 105434439 B | 7/2018 |

(Continued)

OTHER PUBLICATIONS

International Preliminary Report on Patentability issued Dec. 3, 2020, by the International Bureau of WIPO for 3CT/IB2019/054016.
Morgan IG et al.; The epidemics of myopia: aetiology and prevention. Prog Retin Eye Res 2018; 62:134-49; (2017).
Yanxian C et al.; Best practice in myopia control: insights and innovations for myopia prevention and control—a round table discussion. Br J Ophthalmol 2024; 108(7) 913-4; (May 10, 2024).

(Continued)

*Primary Examiner* — Darryl J Collins
(74) *Attorney, Agent, or Firm* — Volpe Koenig

(57) ABSTRACT

A method for preventing or limiting the progression the myopia includes: providing a soft contact lens. The contact lens includes: a solid polymeric component, which is provided for conferring shape and structure on the contact lens and a liquid component which is distributed in the solid component, and which comprises tyrosine, at a concentration between 1 and 200 mg/l. The method further includes putting the soft contact lens on an eye of a patient so as to apply the compound on the eye.

8 Claims, 1 Drawing Sheet

(58) Field of Classification Search
USPC .................................................. 351/159.02
See application file for complete search history.

(56) References Cited

U.S. PATENT DOCUMENTS

| | | | |
|---|---|---|---|
| 4,668,506 A | 5/1987 | Bawa | |
| 5,187,207 A | 2/1993 | Gallas | |
| 5,284,843 A | 2/1994 | Stone et al. | |
| 7,132,567 B2* | 11/2006 | Alberte | C07D 207/12 558/47 |
| 2006/0271027 A1 | 11/2006 | Silvestrini et al. | |
| 2012/0088861 A1 | 4/2012 | Huang et al. | |
| 2014/0036225 A1* | 2/2014 | Chehab | A61K 31/46 351/159.02 |
| 2016/0018671 A1* | 1/2016 | Waite | A61P 37/08 351/159.04 |
| 2016/0338947 A1* | 11/2016 | Leahy | A61K 47/32 |
| 2017/0326088 A1* | 11/2017 | Vidyasagar | A61P 1/00 |
| 2017/0368061 A1 | 12/2017 | Nguyen et al. | |
| 2018/0094137 A1* | 4/2018 | Mackay | C07K 14/78 |

FOREIGN PATENT DOCUMENTS

| | | | |
|---|---|---|---|
| EP | 0834308 A1 | 4/1998 | |
| EP | 2693259 A1 * | 2/2014 | A61K 31/46 |
| JP | S6177822 A | 4/1986 | |
| JP | H09503752 A | 4/1997 | |
| JP | 2003055225 A | 2/2003 | |
| JP | 2004203867 A | 7/2004 | |
| JP | 2005054437 A | 3/2005 | |
| JP | 2005084558 A | 3/2005 | |
| JP | 2005154437 A | 6/2005 | |
| JP | 2010204597 A | 9/2010 | |
| JP | 2013190789 A | 9/2013 | |
| JP | 2014032404 A | 2/2014 | |
| JP | 2015509205 A | 3/2015 | |
| JP | 2018532835 A | 11/2018 | |
| WO | 8901639 A1 | 2/1989 | |
| WO | 2010039939 A1 | 4/2010 | |
| WO | 2016187426 A1 | 11/2016 | |
| WO | 2017055536 A1 | 4/2017 | |
| WO | 2017140846 A1 | 8/2017 | |
| WO | 2017177262 A1 | 10/2017 | |

OTHER PUBLICATIONS

Feldkaemper M and Schaeffel F.; An updated view on the role of dopamine in myopia Experimental Eye Research 2013; 114:106-19; (Feb. 19, 2013).
Thomson K et al.; Effectiveness and safety of topical levodopa in a chick model of myopia. Scientific Reports 2019; 9:18345. doi.org/10.1038/s41598-019-54789-5; (Dec. 4, 2019).
Torii H et al.; Violet light exposure can be a preventive strategy against myopia progression. EBioMedicine 2017; 15:210-9; (Dec. 16, 2016).
DelMonte DW and Kim T.; Anatomy and physiology of the cornea. J Cataract Refract Surg 2011; 37:588-98; (Oct. 29, 2010).
Bodor N, Buchwald P.; Ophthalmic drug design based on the metabolic activity of the eye: soft drugs and chemical delivery systems. AAPS J 2005;7(4) Article 79:E820; (Dec. 7, 2005).
Santana CP et al.; Corneal Permeability and Uptake of Twenty-Five Drugs: Species Comparison and Quantitative Structure—Permeability Relationships. Pharmaceutics 2023, 15, 1646, at 2; (Jun. 2, 2023).
Weng Y et al.; Nanotechnology-based strategies for treatment of ocular disease, Acta Pharmaceutica Sinica 2017; B281, at 281; (Jul. 6, 2016).
Vinciguerra P et al.; Use of amino acids in refractive surgery. Journal of Refractive Surgery 2002; 18:S374-377; (Dec. 14, 2001).
Marx S et al.; Objective analysis of pre-lens tear film stability of daily disposable contact lenses using ring mire projection. Clinical Optometry 2020; 12:203-11; (Dec. 2020).
Wilson SL et al.; Control of scar tissue formation in the cornea: strategies in clinical and corneal tissue engineering. J Funct Biomater 2012; 642:648; (Sep. 18, 2012).
Rusciano D et al.; Free amino acids: an innovative treatment for ocular surface disease. European Journal of Pharmacology 2016; 787: 9-19; (Apr. 14, 2016).
Hirshfield, GS; Why can't I use my skin ointment on my eyes?, American Academy of Ophthalmology, available at https://www.aao.org/eye-health/ask-ophthalmologist-q/why-can-t-i-use-my-skin-ointment-on-my-eyes#:~:text=Answer%3A,outer%20layer%20that%20is%20protective; (Feb. 4, 2022).
Zhou X et al.; Dopamine signaling and myopia development: what are the key challenges. Progress in Retinal and Eye Research 2017; 61:60-71; (Jun. 7, 2017).

* cited by examiner

METHOD FOR PREVENTING OR LIMITING PROGRESSION OF MYOPIA

CROSS REFERENCE TO RELATED APPLICATIONS

This application is a continuation of U.S. patent application Ser. No. 17/057,171, filed Nov. 20, 2020, which is a 371 is a National Stage Entry of PCT/IB2019/054016, filed May 15, 2019, the entire contents of which are incorporated by reference as if fully set forth.

TECHNICAL FIELD

The present invention particularly relates to a soft contact lens which is capable of releasing in a controlled manner an active ingredient which is advantageous in slowing down myopia progression.

The invention is further related to a packaging which comprises a soft contact lens and to processes for producing a soft contact lens.

BACKGROUND

Myopia is a sight defect which is very common and as a result of which the parallel light rays which arrive from outside the eye are not correctly focused on the retina, but instead in front of it.

This sight defect is often a result of an incompletely spherical formation, in particular an elongate formation along the optical axis, of the eyeball.

The onset of myopia generally occurs from infancy and increases with growth. Therefore, there may be noted a progressive increase of the severity of the myopia which tends to increase until a maximum value which changes from person to person.

A widely used instrument for correcting sight defects and in particular ametropias, such as myopia, is contact lenses and, among them, soft contact lenses.

One of the characteristics which make the soft contact lenses particularly valued by users with respect to other types of contact lenses (rigid or semi-rigid ones) is certainly the greater comfort thereof during use once being worn.

This advantageous characteristic is given by the high hydrophilic capacities of the lens which, in containing a relevant percentage of water, allows a greater compatibility between the lens and eye, in addition to a greater deformability of the lens which allows it to adapt better to the surface of the eye.

Soft contact lenses are conventionally produced by means of a process which provides for a first step of obtaining a dry semi-finished product of lenticular form of a polymer material which can in turn be obtained by polymerization of a monomer directly in a mold (injection-molding technique), or by a disc of material which is already polymerized being turned (turning technique).

Independently of the technique used for the preparation thereof, the dry semi-finished product is subsequently hydrated by means of immersion in a saline solution (known as physiological solution), where applicable buffered, formed by approximately 1% by weight of sodium chloride in water. The polymer material used is typically provided with optimum hydrophilic properties, for example, a polymer admixture based on HEMA or a silicone-based polymer, so that a relevant quantity of saline solution between 25% and 75% is absorbed in the dry semi-finished product.

The absorption of the liquid component, in addition to conferring on the lens the above-mentioned characteristics of compatibility and softness, also involves a physical expansion of the dry semi-finished product, both radial and linear, thereby determining both the final dimensions of the contact lens and the optical properties thereof.

The contact lens obtained in this manner thus comprises a solid component which defines the structural portion of the lens and which is constituted by the polymer material and a liquid component which is constituted by the saline solution which is distributed in a substantially uniform manner in the solid component.

SUMMARY

The problem addressed by the present invention is to provide a soft contact lens which is produced in such manner that the use thereof aids the delay of the myopia progression of a user.

This problem is solved by the present invention by means of a soft contact lens which is produced according to the appended claims.

In a first aspect thereof, therefore, the present invention relates to a soft contact lens comprising a solid component, based on a polymer, and a liquid component which is distributed in the solid component and which comprises an effective quantity of a compound selected from the group formed by tyrosine, derivatives of tyrosine, precursors of tyrosine and dopamine.

In this manner, the contact lens is capable of gradually releasing into the eye over an extended period of time a suitable and predetermined quantity of a compound which delays the myopia progression.

In a second aspect, the invention further relates to a packaging comprising a soft contact lens which is produced according to the preceding aspect and which is immersed in a preservation solution, comprising at least one of the compounds selected from the group formed by tyrosine, derivatives of tyrosine, precursors of tyrosine and dopamine at a concentration which is at least equal to the one present in the liquid component of the soft contact lens.

The release of the active compound present in the liquid component of the soft contact lens into the preservation liquid is thereby prevented during the time period which occurs between the packaging thereof and the use thereof by a user.

In a third aspect thereof, the present invention further relates to a process for producing a soft contact lens according to the first aspect, wherein there are provided the steps of:
  providing a dry semi-finished product of the soft contact lens which is based on a polymer and which is intended to form a solid component of the soft contact lens, and
  hydrating the dry semi-finished product by means of immersion in an aqueous solution which comprises an effective quantity of a compound selected from the group formed by tyrosine, derivatives of tyrosine, precursors of tyrosine and dopamine, so as to bring a liquid component which contains this compound to the solid component and to thereby obtain the soft contact lens according to the first aspect.

In a fourth aspect thereof, the present invention further relates to an additional process for producing a soft contact lens according to the first aspect, wherein there are provided the steps of:

providing a dry semi-finished product of the soft contact lens which is based on a polymer and which is intended to form a solid component of the soft contact lens, hydrating the dry semi-finished product by means of immersion in an aqueous solution so as to bring a liquid component to the solid component and to thereby obtain a soft contact lens, packaging the soft contact lens inside a container in which it is immersed in a preservation solution, subjecting the packaging containing the soft contact lens to a sterilizing processing operation in an autoclave.

Both these processes advantageously allow the contact lens of the invention to be obtained in a simple and effective manner.

In the first process, the aqueous solution which comprises the compound which is capable of delaying the myopia progression is introduced inside the dry semi-finished product by being distributed uniformly in the polymer and thereby forming the liquid component of the contact lens.

In the second process, the contact lens is placed in contact with a preservation solution which comprises the compound which is capable of delaying the myopia progression when it is already formed. In this case, however, there may also be observed the introduction of the compound into the lens and the uniform distribution thereof in the liquid component of the lens. This action is particularly promoted by the action of heat to which the contact lens and the preservation solution are subjected during the sterilization processing operation and by the fact that the compounds in question have relatively low molecular weights so that the passage thereof through the porosity of the polymer which forms the soft contact lens is not substantially impeded by the dimensions thereof.

In at least one of the above aspects, the present invention may have one or more of the following preferred features.

The solid component of the soft contact lens is provided for conferring shape and structure on the contact lens and is preferably produced from a hydrophilic polymer, such as, for example, HEMA, or from silicone.

The soft contact lens of the present invention may, however, be produced by using any other polymer or copolymer which is suitable for this purpose and which is normally used in this field.

The liquid component of the soft contact lens is capable of promoting the compatibility between the lens and eye of a user of the contact lens.

The liquid component is preferably distributed in a substantially uniform manner inside the solid component.

The liquid component is an aqueous solution and is preferably a saline solution, with a suitable concentration of NaCl, for example, of approximately 0.9 g/l.

The liquid component preferably has an osmolarity between 150 and 350 mOsm, preferably between 280 and 310 mOsm.

In a preferred embodiment, the liquid component also comprises a suitable amount of lubrication compounds. Examples of suitable lubrication compounds comprise polyvinyl alcohols, polysaccharides, such as, for example, trehalose, derivatives of cellulose, such as, for example, hydroxy propyl cellulose, methyl cellulose and carboxy methyl cellulose, and polyethers, such as, for example, polyethylene glycols. These compounds may be present in the liquid component at a concentration between approximately 0.1% and approximately 5%.

In a preferred embodiment, the liquid component further comprises regulating compounds for the rheological properties which are capable of conferring on the liquid component viscoelasticity characteristics which are as similar as possible to those of tear fluid.

In a preferred embodiment, the regulating compounds for the rheological properties comprise hyaluronic acid or a salt thereof or a polysaccharide, such as galacto xyloglucan which is extracted from tamarind seeds (TSP), having a suitable molecular weight, for example, between 500 KDalton and 1000 KDalton.

As set out above, the liquid component comprises an effective quantity of a compound which is selected from the group formed by tyrosine, derivatives of tyrosine, precursors of tyrosine and dopamine.

Preferably, the concentration of this compound in the liquid component is substantially constant in the various regions of the contact lens. In particular, this concentration varies to an extent not greater than 20% between various regions of the contact lens.

Dopamine is a catecholamine, the molecular structure of which is illustrated in the formula (I) depicted below.

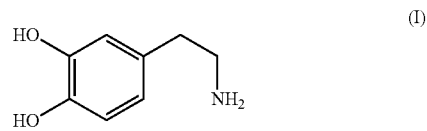 [SMILES: NCCc1ccc(O)c(O)c1]

Dopamine is a neurotransmitter and, inside the eye, it is involved in the mediation of various functions, including the development of the retina tissue, the transmission of the vision signal and the development of the correct refraction.

Furthermore, dopamine has a relevant influence on the control of the growth of the eyeball. In particular, it has been observed that the action thereof delays the axial growth of the eyeball, thereby slowing down the possible extension thereof along the optic axis, which is a primary cause of myopia.

As a result of this particular action, it may be considered that the presence of an adequate concentration of dopamine in the eye is capable of delaying effectively the progression of myopia.

In fact, it has been shown how the progression of myopia may be delayed by a high activity in the open air, probably via the action of the violet component of the sunlight (wavelength: 360-400 nm). The violet radiation would act by activating the EGR1 gene, which is a suppressor of myopia, and by stimulating the production of dopamine inside the retina.

The Applicant has verified how an effective quantity of dopamine can be released in the eye by a soft contact lens in the liquid component of which there is present a suitable concentration of dopamine or a precursor thereof.

The presence of the dopamine in the liquid component of the contact lens allows a gradual and continuous release over time which may facilitate the effective action of the dopamine inside the eye.

In this manner, the contact lens may advantageously be used not only for correcting myopia but also for preventing or at least limiting the deterioration of this sight defect.

In a first preferred embodiment, the liquid component of the soft contact lens contains a precursor of dopamine.

In this manner, there may be used a compound which, during production of the contact lens, may be managed and used in a simpler manner than dopamine.

In particular, the precursor of dopamine is preferably tyrosine or a derivative of tyrosine or a precursor of tyrosine.

Tyrosine is a polar amino acid, the molecular structure of which is illustrated in the formula (II) which is depicted below.

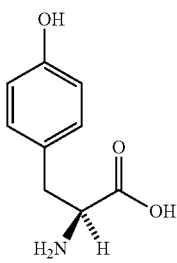

(II)

Tyrosine comprises three isomers (para, meta and ortho-tyrosine), among which the most common is the para isomer (illustrated above in the formula (II)). Furthermore, tyrosine is a molecule which is optically active and which has two enantiomers, L and D.

In nature, the enantiomer L (L-tyrosine) which represents one of the 20 natural amino acids is most common.

The term tyrosine is intended to be understood to be all the isomers and the enantiomers of tyrosine, preferably the enantiomer L of para-tyrosine.

Tyrosine may give rise to various compounds, and in particular, to dopamine which acts to prevent the progression of myopia in the terms set out above.

Examples of derivatives of tyrosine are constituted by phosphotyrosine and sulphotyrosine, in which the tyrosine is modified by the addition of a phosphoric group and a sulfuric group, respectively.

These derivatives of tyrosine are more polar with respect to tyrosine and may advantageously give rise to a slower and more gradual release of this compound in the eye.

An example of a precursor of tyrosine is constituted by phenylalanine, the molecular structure of which is depicted in the formula (III) set out below.

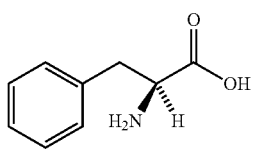

(III)

In a preferred form of the invention, tyrosine is present in the liquid component of the soft contact lens at a concentration greater than 1 mg/l.

Preferably, the concentration of tyrosine in the liquid component of the soft contact lens is between 1 and 500 mg/l, more preferably it is between 1 and 200 mg/l, and in a greatly preferred manner it is between 10 and 100 mg/l.

In another preferred embodiment, the liquid component of the soft contact lens according to the invention comprises an effective quantity of an antioxidant compound.

Preferably, the antioxidant compound comprises vitamin E or vitamin B2 or an admixture thereof.

Vitamin E is a liposoluble antioxidant and has an important role in the prevention of oxidation of the fatty polyunsaturated acids, blocking the action of free radicals.

There exist 8 types of vitamin E, tocotrienols and tocopherols. Of these, the vitamin compound which is most active and powerful is a-tocopherol.

Vitamin B2 (riboflavin) also has an antioxidant action.

The presence of antioxidant compounds, such as vitamin E or B2, allows a reduction in any negative effects of the action of sunlight, which is advantageous, on the one hand, for promoting the correct production of dopamine, but potentially damaging for the processes of cellular oxidation which are triggered in particular by the ultraviolet component thereof.

Preferably, there is present in the liquid component of the soft contact lens according to the invention a concentration of a-tocopherol of at least 1 mg/l, for example, between 1 and 500 mg/l, more preferably between 1 and 100 mg/l, even more preferably between 2 and 20 mg/l.

Preferably, there is present in the liquid component of the soft contact lens according to the invention a concentration of riboflavin of at least 1 μg/l, for example, between 1 and 1000 μg/l, more preferably between 1 and 100 μg/l, even more preferably between 2 and 50 μg/l.

BRIEF DESCRIPTION OF THE DRAWINGS

The features of the invention will be better appreciated from the following detailed description of a preferred embodiment thereof which is illustrated by way of non-limiting example with reference to the appended drawings, in which.

DETAILED DESCRIPTION OF THE PREFERRED EMBODIMENTS

In the appended Figures, a soft contact lens produced according to the present invention is generally designated 4.

The soft contact lens 4 is preferably a corrective lens but generally may be of any known type.

The soft contact lens 4 is produced according to the following process.

In a first step, there is produced according to techniques which are generally conventional per se (by injection-molding or by turning) a dry semi-finished product of polymer material which is capable of conferring on the lens the final structure and formation. The dry semi-finished product may be obtained from a polymer admixture based on HEMA or from any other polymer or copolymer which is suitable for this purpose or which is normally used in the field, for example, a polymer based on silicone.

In a subsequent processing step, the dry semi-finished product is hydrated by immersion in an aqueous solution which is advantageously agitated so that there is absorbed in the solid component in a substantially uniform manner a liquid component which promotes the comfortable use of the contact lens and therefore the compatibility thereof with the eye of a user.

At the end of the hydration step, the soft contact lens 4 is then ready for being packaged and subsequently sterilized by means of processing in an autoclave at approximately 120° C. for a time of approximately 20 minutes.

Figure 1:
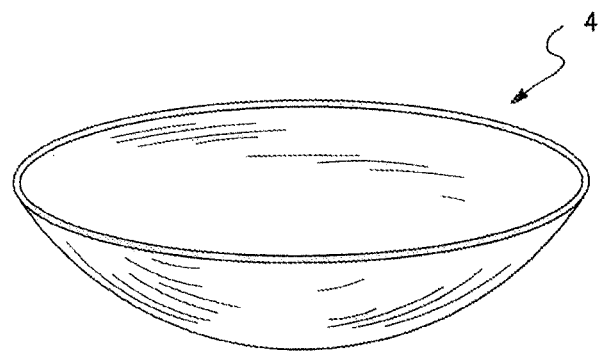
FIG. 1 is a schematic perspective Figure of a contact lens produced according to the present invention.
Figure 2:
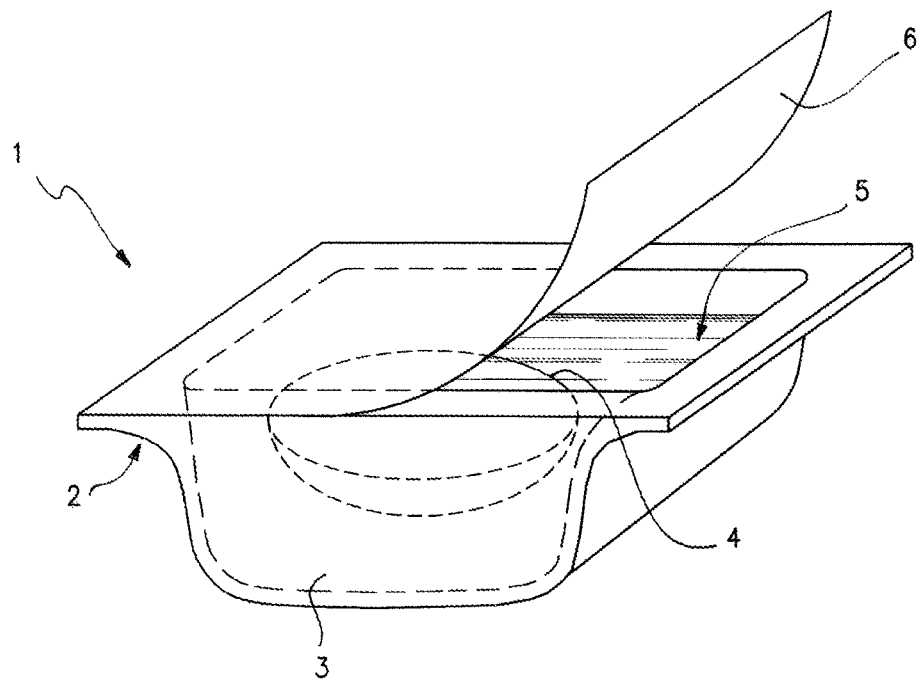
FIG. 2 is a schematic perspective view of a packaging for storing and preserving the contact lens of FIG. 1.

FIG. 2 illustrates a packaging for storing and preserving the soft contact lens 4, which is generally designated 1. The packaging 1 comprises a support 2 which is produced, for example, from plastics material which is shaped so as to define a container 3, inside which the soft contact lens 4 is immersed in a preservation solution 5.

The packaging 1 further comprises a membrane 6 which is connected, for example, by means of thermowelding, to a peripheral edge of the support 2 so as to seal the container 3 and to prevent the discharge of the soft contact lens 4 or the preservation solution 5.

For greater clarity, the membrane 6 is illustrated in FIG. 2 in a partially raised position.

According to a first aspect of the invention, the aqueous solution in which the dry semi-finished product is immersed for the hydration processing comprises an effective quantity of a compound selected from the group formed by tyrosine, derivatives of tyrosine, precursors of tyrosine and dopamine.

In the preferred example described here, the aqueous solution comprises an effective quantity of L-tyrosine, for example, at a concentration between 10 and 100 mg/l, a quantity of sodium chloride of approximately 0.9 g/l and a concentration of vitamin E between 1 and 100 mg/l and/or a concentration of vitamin B2 between 1 and 100 µg/l. Optionally, the aqueous solution may comprise lubrication compounds, such as, for example, polyvinyl alcohols, or regulating compounds for the rheological properties, such as, for example, sodium hyaluronate or galacto xyloglucan which is extracted from tamarind seeds at a concentration of approximately 0.2%.

In addition, the aqueous solution may comprise a surfactant agent, a disinfecting agent, for example, disodium EDTA, at a quantity of approximately 0.1%, a buffering agent, such as, for example, sodium phosphate, so as to maintain an overall pH of approximately from 7.3 to 7.4.

The soft contact lens 4 which is thereby obtained therefore comprises, at the level of a conventional lens, a solid component which is substantially constituted by the polymer material and a liquid component which is distributed in a substantially uniform manner in the solid component in which the liquid component has substantially the same composition as the aqueous solution in which the dry semi-finished product has been immersed.

The portion of liquid component present in the soft contact lens is between 25% and 75%.

In an alternative production process, the contact lens 4 may be hydrated with an aqueous solution which does not have any L-tyrosine and vitamin E and/or B2 while these compounds may instead be present in the above-indicated concentrations in the preservation solution 5 in which the contact lens 4 is immersed, once it has been formed, for the packaging thereof. In this case, the introduction of the L-tyrosine and the vitamins E and/or B2 in the liquid component of the contact lens 4 is carried out during the sterilization step of the packaging 1.

According to another aspect of the invention, the preservation solution 5 comprises a concentration of L-tyrosine which is at least equal to that present in the liquid component of the soft contact lens 4.

If the second production process is used, the preservation solution 5 will naturally have a concentration of L-tyrosine and vitamin E and B2 which is substantially identical to the liquid component of the contact lens 4.

The soft contact lens 4, once it has been removed from the packaging 1 and put in place by the user, releases slowly and gradually into the eye the L-tyrosine which at a suitable time gives rise to dopamine which carries out the action thereof of limiting and preventing the progression of myopia.

Furthermore, the soft contact lens 4 slowly and gradually releases into the eye of the user the antioxidant compound vitamin E and/or vitamin B2 which prevents the damaging effects of exposure to sunlight which is advantageous in retarding the progression of myopia.

The contact lenses according to the invention may be produced so as to be replaced at a monthly frequency or at a greater frequency, for example, at a daily rate, weekly rate or bi-weekly rate, in accordance with the polymer material which is preselected and the characteristics thereof for retaining the liquid component.

Preferably, the contact lens is provided for weekly or daily replacement.

The present invention thereby solves the problem set out above by providing a soft contact lens which is capable of preventing or at least limiting the progression of myopia.

Furthermore, at the same time it affords a number of other advantages, including the fact of allowing the production of this soft contact lens by means of a production process which is simple and inexpensive.

The invention claimed is:

1. A method comprising:
   providing a soft contact lens comprising:
      a solid polymeric component, which is provided for conferring shape and structure on the contact lens; and
      a liquid component, provided for preventing or limiting progression of myopia, which is distributed in the solid component, and which comprises tyrosine at a concentration between 1 and 200 mg/L and which further comprises an effective quantity of regulating compounds for regulating rheological properties of the liquid component, the regulating compounds comprising hyaluronic acid or a salt thereof or a polysaccharide, wherein the polysaccharide is galacto xyloglucan, which is extracted from tamarind seeds (TSP); and
   putting the soft contact lens on an eye of a patient so as to apply the liquid component on the eye.

2. The method according to claim 1, further comprising preventing or limiting the progression of myopia via the liquid component acting on the eye.

3. The method according to claim 1, wherein the liquid component of the contact lens further comprises an effective quantity of an antioxidant compound.

4. The method according to claim 3, wherein the antioxidant compound comprises vitamin E or vitamin B2 or admixtures thereof.

5. The method according to claim 4, wherein the vitamin E, when present, has a concentration between 1 and 500 mg/L, and the vitamin B2, when present, has a concentration between 1 and 1000 µg/L.

6. The method according to claim 4, wherein the vitamin E, when present, has a concentration between 1 and 100 mg/l, and the vitamin B2, when present, has a concentration between 1 and 100 µg/l.

7. The method according to claim 4, wherein the vitamin E, when present, has a concentration between 2 and 20 mg/l, and the vitamin B2, when present, has a concentration between 2 and 50 µg/l.

8. The method according to claim 1, wherein the concentration of tyrosine in the liquid component of the contact lens is between more than 10 mg/L and 100 mg/L.

* * * * *